(12) United States Patent
Gao (10) Patent No.: US 8,764,025 B1
(45) Date of Patent: Jul. 1, 2014

(54) SELF-LOCKING INTERNAL ADAPTER WITH FREE GUIDE MECHANISM

(75) Inventor: Hua Gao, Fox Point, WI (US)

(73) Assignee: Bradshaw Medical, Inc., Kenosha, WI (US)

( * ) Notice: Subject to any disclaimer, the term of this patent is extended or adjusted under 35 U.S.C. 154(b) by 496 days.

(21) Appl. No.: 13/229,454

(22) Filed: Sep. 9, 2011

(51) Int. Cl.
B23B 31/07 (2006.01)

(52) U.S. Cl.
USPC ............................ 279/30; 279/22; 279/905

(58) Field of Classification Search
CPC .... B23B 31/1071; B23B 31/22; B23B 31/008
USPC ............. 279/30, 22, 76, 75, 74, 82, 905, 904; 81/438, 489, 177.85, 177.1, 177.9
See application file for complete search history.

(56) References Cited

U.S. PATENT DOCUMENTS

| | | | | |
|---|---|---|---|---|
| 1,307,937 | A | | 6/1919 | Straub |
| 2,289,583 | A | | 7/1942 | Malone |
| 2,838,266 | A | * | 6/1958 | Rees .......................... 248/354.1 |
| 3,039,781 | A | * | 6/1962 | Bilz ............................... 279/75 |
| 3,398,965 | A | * | 8/1968 | Cox ............................... 279/30 |
| 3,521,895 | A | * | 7/1970 | Smith ............................. 279/22 |
| 4,412,764 | A | * | 11/1983 | Wawrzyniak ................. 408/226 |
| 5,464,229 | A | * | 11/1995 | Salpaka .......................... 279/30 |
| 5,741,263 | A | | 4/1998 | Umber et al. |
| 5,928,241 | A | | 7/1999 | Menut et al. |
| 6,059,296 | A | * | 5/2000 | Baeder ........................... 279/20 |
| 6,179,302 | B1 | | 1/2001 | Gauthier et al. |
| 6,901,826 | B2 | * | 6/2005 | Huang ........................ 81/177.2 |
| 7,086,313 | B2 | | 8/2006 | Cantlon |
| 7,325,811 | B2 | * | 2/2008 | Hartmann et al. .............. 279/19 |
| 7,500,811 | B2 | * | 3/2009 | Pfob ............................... 408/56 |
| 7,810,817 | B1 | | 10/2010 | Gao |

FOREIGN PATENT DOCUMENTS

DE 4105515 A1 * 8/1992

* cited by examiner

*Primary Examiner* — Eric A Gates
*Assistant Examiner* — Paul M Janeski
(74) *Attorney, Agent, or Firm* — Absolute Technology Law Group, LLC (57) ABSTRACT

An internal adapter for use in handles for interchangeable orthopedic tools contains a collar assembly, house assembly, retaining ring, spring and driver assembly. A plurality of securing ball mechanisms releasably secure an orthopedic tool in the adapter, while a configuration of chamfered surfaces centrally stabilize the tool. A plurality of guiding chamfers located in a shaft driver assembly rotationally secures the orthopedic tool.

20 Claims, 9 Drawing Sheets

SELF-LOCKING INTERNAL ADAPTER WITH FREE GUIDE MECHANISM

FIELD OF INVENTION

The present invention relates to the field of medical devices, and more specifically to a self-locking internal adapter for securing medical tools.

TERMS OF ART

As used herein, the term "adapter" refers to a component of an orthopedic tool handle which engages a tool.

As used herein, the term "chamfer" refers to a beveled, angled or tapered edge which engages the edge of a second component to create a secured junction.

As used herein, the terms "flattened portion" or "partially flattened portion" refer to a cylindrical surface having an area with a curvature less than that of the cylindrical curvature. A flattened or partially flattened portion may contain a single area or multiple areas of lesser curvature.

BACKGROUND

Adjustment tools are used in orthopedic surgery to tighten and adjust mechanical components within orthopedic devices. For example, screwdrivers, spreaders, pliers, hammers, cutters and other tools may be used to adjust screws, pins, rods and other orthopedic devices. The adjustment tools for adjusting these orthopedic devices must be highly stable to allow for precise adjustments, and many types of adjustments may be needed.

In order to save space on an operating room instrument table or in a sterilization kit, different orthopedic tools may be designed to be interchangeable with a single handle. For example, it is known in the art to fashion tools of varying lengths with shafts that may be inserted into a single tool handle.

As a result, a typical orthopedic tool may actually be a system of three components: a handle, an adapter and a tool. Generally, the handle and the adapter are structurally integrated and permanently attached to other other. Tools are adapted for insertion into the adapter.

Adapters for securing medical tools, specifically medical tools with a square or hexagonal shaft, to handles are known in the art. Every adapter has some sort of channel or orifice to receive the tool, and a locking mechanism to secure the tool in place. The function and simplicity of operating the locking mechanism are critical. Even incremental improvements in a locking mechanism can be critical to the outcome of a surgery.

Tools must be compact to allow an orthopedic surgeon to perform adjustments to orthopedic devices and other tasks within the confined space of various body regions.

Tools must also be versatile, and it is desirable to have as many tools as possible adapted for use with a single adapter and handle.

Adapter components are likely to come in contact with bodily fluids and other contaminants during medical procedures. Any contours, grooves and other hard-to-reach surfaces need to be carefully cleaned and sterilized. Exposed attachment components are also more likely to be bumped or inappropriately forced in an attempt to attach a medical tool. As a result, exposed attachment components are frequently damaged.

It is desirable to have an adapter for securing medical tools to handles which reduce the number of exposed components and surfaces.

It is desirable to have an apparatus for securing and grasping tools which is as compact as possible so that surgeons can operate within the limited spaces and contours of various regions of the body.

It is critical to have an adapter for securing medical tools in place as effectively and simply as possible.

SUMMARY OF THE INVENTION

The present invention is an internal adapter for use in handles for interchangeable orthopedic tools. A plurality of securing ball mechanisms releasably secure an orthopedic tool in the adapter, while a configuration of chamfered surfaces centrally stabilize the tool. A plurality of guiding chamfers located in a shaft driver assembly rotationally secures the orthopedic tool.

DETAILED DESCRIPTION OF INVENTION

For the purpose of promoting an understanding of the present invention, references are made in the text to exemplary embodiments of an internal adapter for orthopedic tools, only some of which are described herein. It should be understood that no limitations on the scope of the invention are intended by describing these exemplary embodiments. One of ordinary skill in the art will readily appreciate that alternate but functionally equivalent structures and materials may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Figure 1:
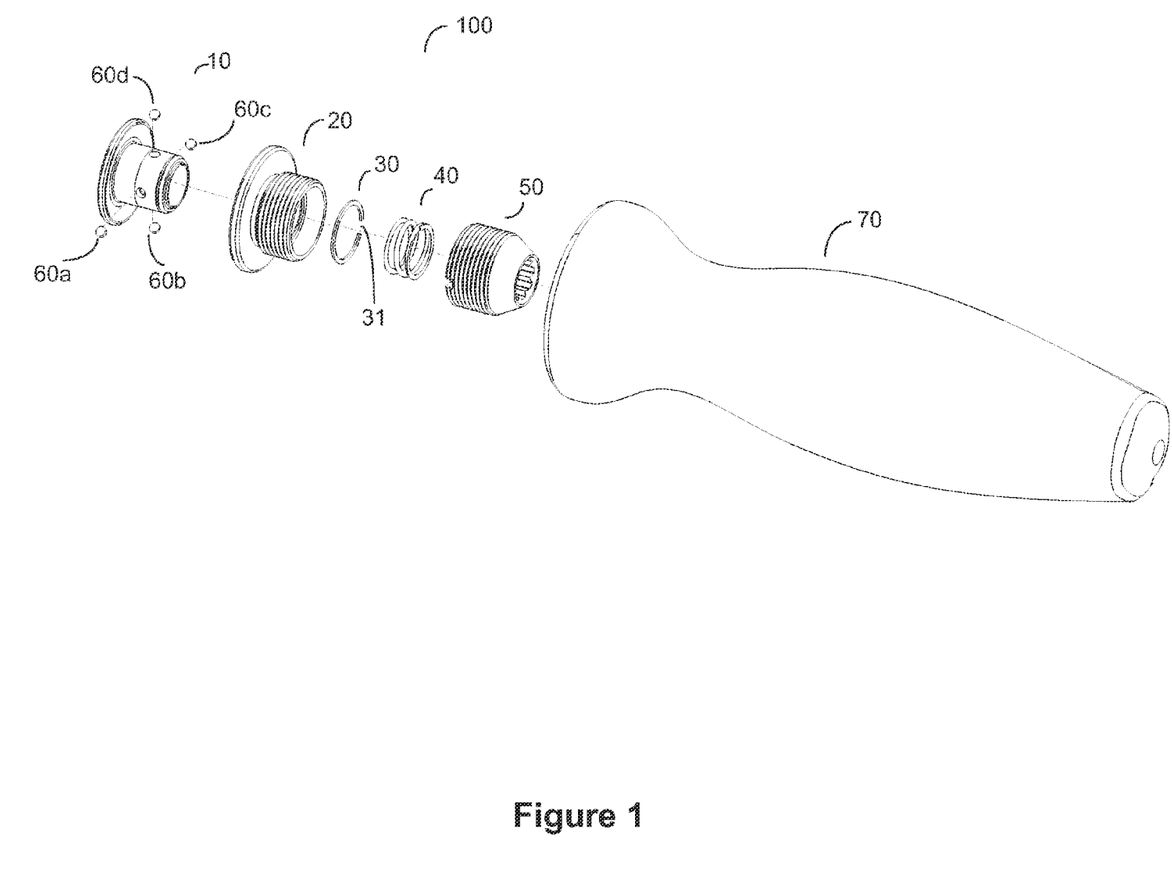
FIG. 1 is an exploded view of an exemplary embodiment of an internal adapter.

FIG. 1 is an exploded view of an exemplary embodiment of self-locking internal adapter 100. Internal adapter has collar assembly 10, house 20, retaining ring 30, spring 40, shaft driver assembly 50, and securing balls 60a, 60b, 60c, 60d. When assembled, internal adapter 100 is configured to be secured in handle 70.

As illustrated in FIG. 1, collar assembly 10, house 20, retaining ring 30, spring 40 and shaft driver assembly 50 are shown as separately manufactured components. In further exemplary embodiments, two or more of collar assembly 10, house 20, retaining ring 30, spring 40 and shaft driver assembly 50 integrally manufactured or machined. In still further exemplary embodiments, one or more of collar assembly 10, house 20, retaining ring 30, spring 40 and shaft driver assembly 50 may be integrally manufactured with handle 70.

In the exemplary embodiment shown, handle 70 is a countered driver handle. In further exemplary embodiments, internal adapter 100 may be used with a torque driver, ratcheting driver, or other driver known in the art.

As illustrated in FIG. 1, retaining ring 30 has gap 31. In further exemplary embodiments, retaining ring 30 may be a complete ring without gaps.

Figure 2A:
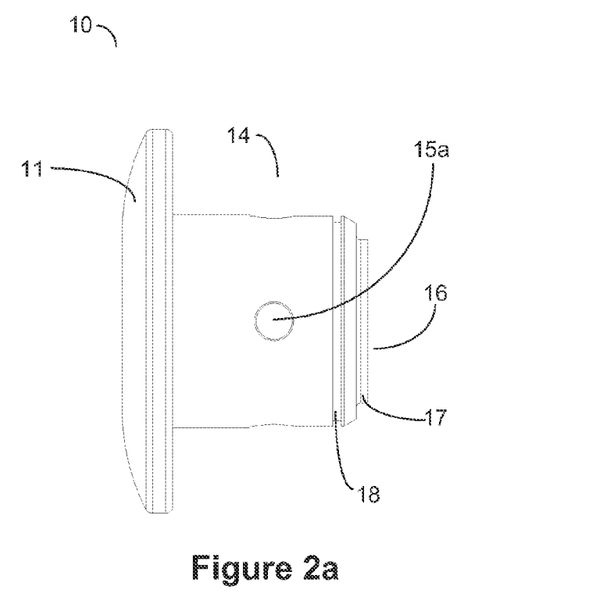
FIGS. 2a and 2b illustrate an exemplary embodiment of a collar assembly.
Figure 2B:
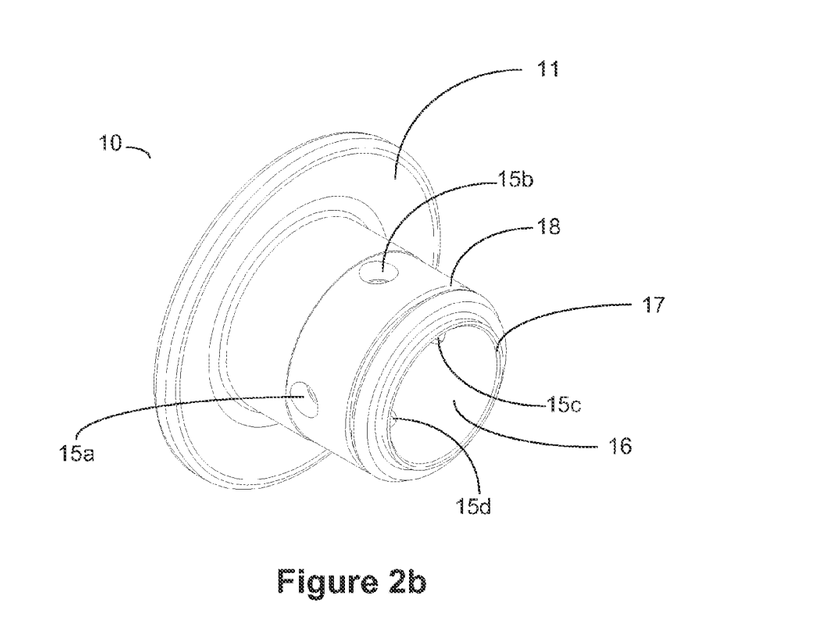

FIGS. 2a and 2b illustrate an exemplary embodiment of collar assembly 10. Collar assembly 10 contains external collar base 11 and tubular sliding portion 14, with tool receiving channel 16 extending the length of collar assembly 10. In the exemplary embodiment shown, tubular sliding portion 14 contains securing ball apertures 15a, 15b 15c, 15d. Securing ball apertures 15a, 15b, 15c, 15d are equidistant and symmetrically arranged around tubular sliding portion 14.

In further exemplary embodiments, tubular sliding portion 14 may contain additional securing ball apertures. While equidistant and symmetrically arranged securing ball apertures provides for greater securing and stability, in further exemplary embodiments, securing ball apertures may be asymmetrically arranged and positioned at varying distances around tubular sliding portion 14.

Securing ball apertures 15a, 15b, 15c, 15d contain a contoured inner surface which creates a diameter smaller than the diameter of securing balls 60a, 60b, 60c, 60d (not shown) at the innermost edge of securing ball apertures 15a, 15b, 15c, 15d. Securing balls 60a, 60b, 60c, 60d (not shown) are therefore freely rotatable within securing ball apertures 15a, 15b, 15c, 15d but may not pass through securing ball apertures 15a, 15b, 15c, 15d. In further exemplary embodiments, securing ball apertures 15a, 15b, 15c, 15d may contain a lip, rim, ridge or other structure which narrows the diameter of the innermost edge of securing ball apertures 15a, 15b, 15c, 15d to prevent securing balls 60a, 60b, 60c, 60d (not shown) from passing through.

FIGS. 2a and 2b also show tool receiving channel 16 extending the length of collar assembly 10. In the exemplary embodiment illustrated, tool receiving channel 16 is round tubular with a smooth surface and consistent internal diameter. In further exemplary embodiments, tool receiving channel may contain projections or grooves or may have an inconsistent internal diameter to accommodate a specifically manufactured tool.

The rear end of tubular sliding portion 14 contains protuberance 17 and groove 18, both of which span the external circumference of tubular sliding portion 14.

Figure 3:
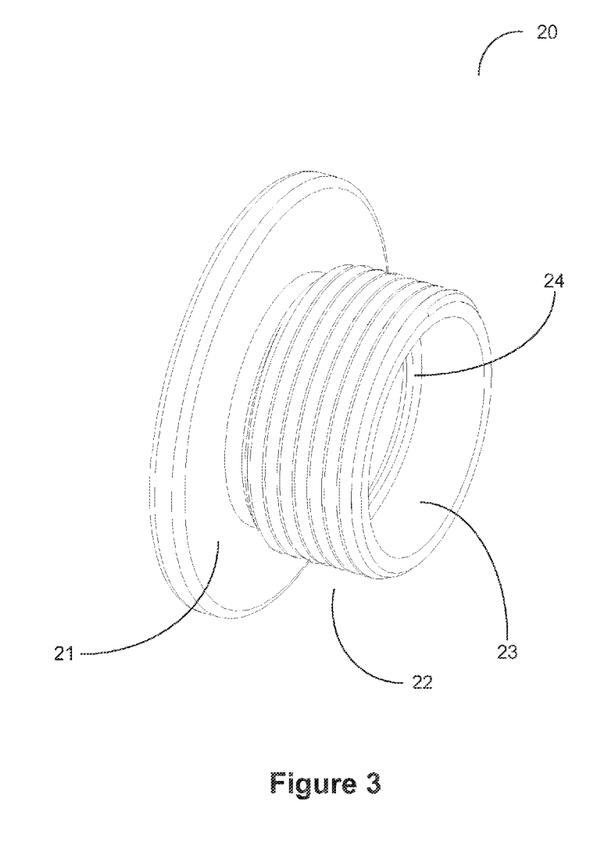
FIG. 3 is an exemplary embodiment of a house assembly.

FIG. 3 is an exemplary embodiment of house 20. As shown in FIG. 3, house 20 contains external house base 21 with threaded handle-engaging stem 22. Interior collar channel 23 contains retaining ring securing protuberance 24 and extends the length of house 20.

Figure 4A:
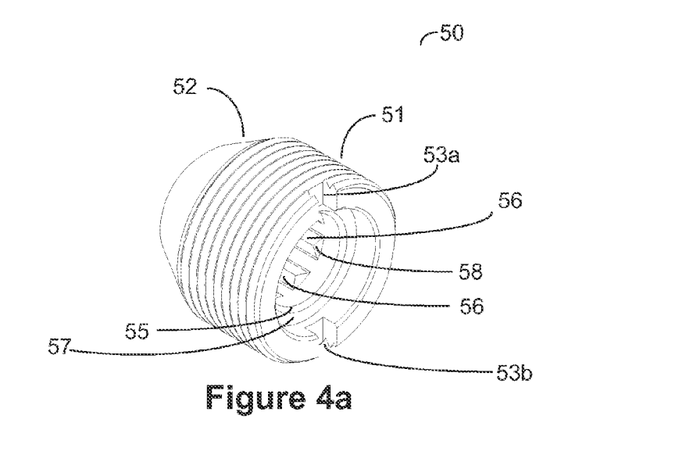
FIGS. 4a, 4b and 4c illustrate an exemplary embodiment of a shaft driver assembly.
Figure 4B:
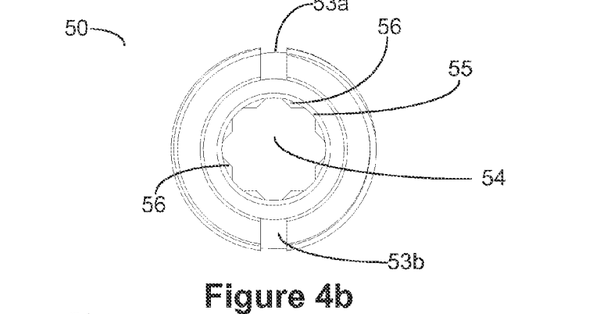
Figure 4C:
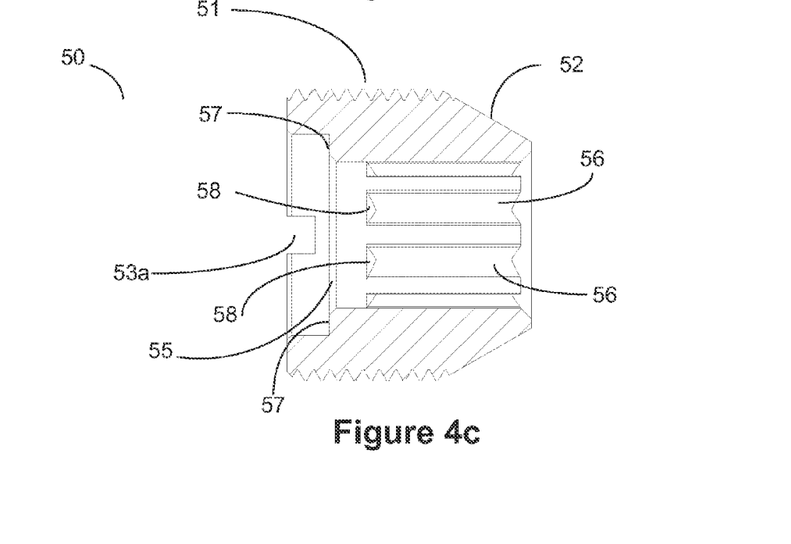

FIGS. 4a, 4b and 4c illustrate an exemplary embodiment of shaft driver assembly 50. Shaft driver assembly 50 has front threaded portion 51 with tapered rear portion 52. Front threaded portion 51 has apertures 53a, 53b. Tool guiding channel 54 extends the length of shaft driver 50.

As illustrated in FIGS. 4a, 4b and 4c, tool guiding channel 54 is primarily round tubular with a smooth internal surface at the front of shaft driver 50. The diameter of tool guiding channel 54 decreases at chamfer 55, creating interior lip 57. Chamfer 55 transitions tool guiding channel 54 to a narrower diameter which includes guiding chamfers 56. In the exemplary embodiments shown, tool guiding channel 54 contains eight double square guiding chamfers 56. In further exemplary embodiments, guiding chamfers may be hexagonal or other configuration, and tool guiding channel 54 may contain more or fewer guiding chamfers 56 to correspond to a guiding chamfer configuration.

As shown in FIGS. 4a and 4c, guiding chamfers 56 do not start at the edge of chamfer 55 and have leading transition chamfer 58. As will be illustrated in FIGS. 8a, 8b and 8c, the proportional distance of leading transition chamfer 58 of guiding chamfers 56 from chamfer 55 is a critical dimension.

Figure 5:
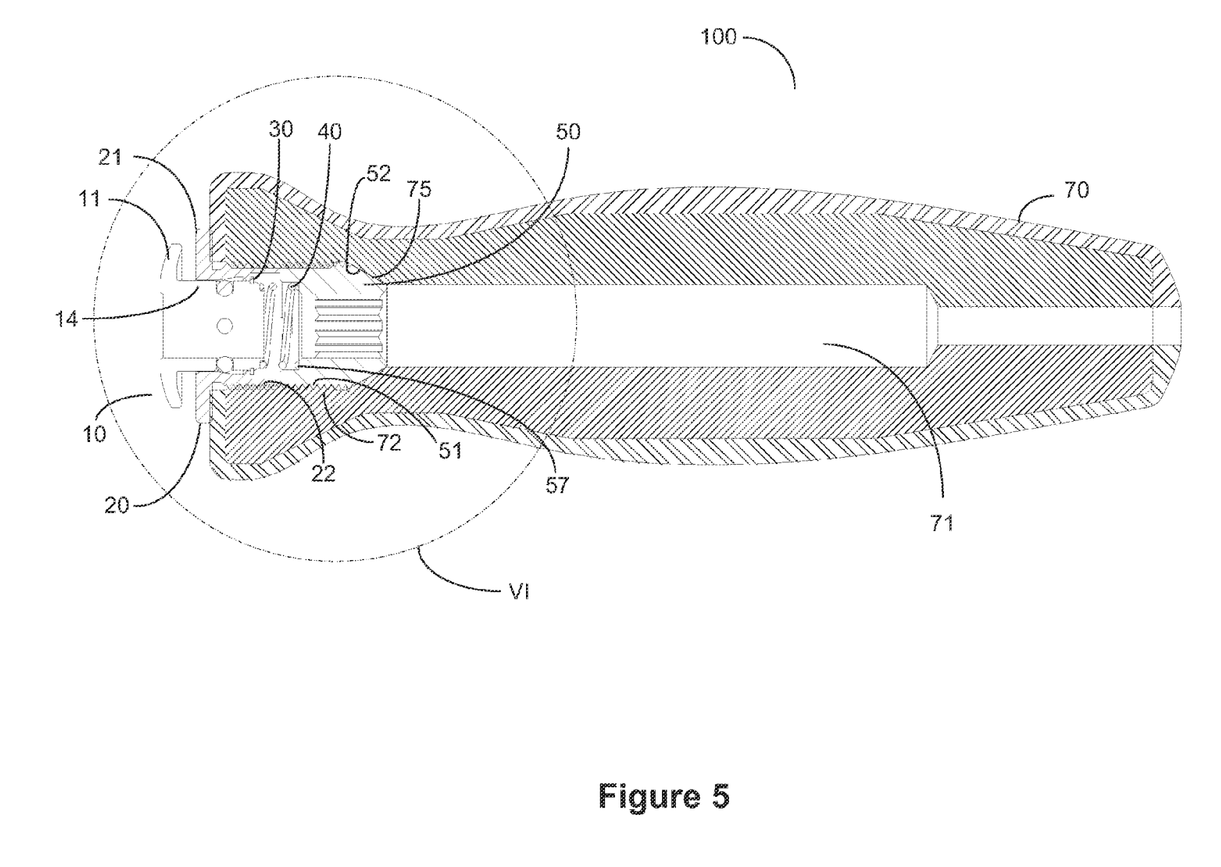
FIG. 5 is a cross-sectional view of an exemplary self-locking internal adapter with free guide mechanism.

FIG. 5 is a cross-sectional view of an exemplary embodiment of an assembled self-locking internal adapter 100. As illustrated in FIG. 5, handle 70 has internal handle cavity 71 with front threaded portion 72. The threads of front threaded portion 72 correspond to the threads of threaded handle-engaging stem 22 and front threaded portion 51 to secure self-locking internal adapter 100 within internal handle cavity 71. In further exemplary embodiments, self-locking internal adapter 100 may be configured to secure to internal handle cavity 71 through any other means known in the art, including, but not limited to, adhesives, pins, locking mechanisms, brackets, screws, contours, friction-fit components, and combination of these structures and devices. In still further exemplary embodiments, self-locking internal adapter 100 may be an integral component of handle 70.

In the exemplary embodiment shown, handle 70 is a standard drive handle. However, in further exemplary embodiments, handle 70 may be any handle known in the art to receive orthopedic tools, including, but not limited to, torque-limiting handles and ratcheting handles.

As illustrated in FIG. 5, external house base 21 and external collar base 11 are the only components of self-locking internal adapter 100 which project outside of handle 70. In some exemplary embodiments, only external collar base 11 may project outside of handle 70. Collar assembly 10 is showed slidingly engaged with house 20, with tubular sliding portion 14 of collar assembly 10 inside interior collar channel 23 (not shown) of house 20.

In the exemplary embodiment shown in FIG. 5, internal handle cavity 71 also contains tapered rear portion 75 which corresponds to tapered rear portion 52 of shaft driver assembly 50. The tapered engagement of shaft driver assembly 50 with handle 70 centers internal adapter 100 and therefore a tool.

Figure 6:
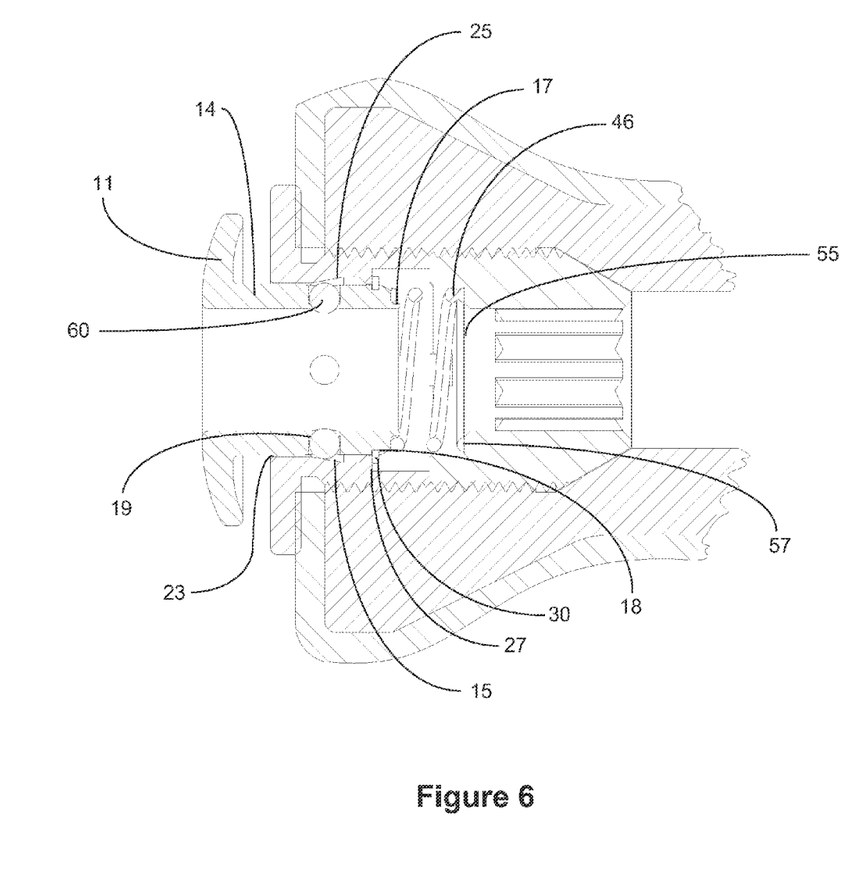
FIG. 6 is an exemplary embodiment of the locking and securing mechanisms of a self-locking internal adapter.

FIG. 6 is an exemplary embodiment of the self-locking mechanism of internal adapter 100. As illustrated in FIG. 6, securing balls 60 are contained within securing ball apertures 15, with interior collar channel 23 of house 20 creating a cover over securing ball apertures 15 to prevent securing balls 60 from disengaging securing ball apertures 15. Contoured inner surface 19 of securing ball apertures 15 prevents securing balls 60 from slipping through securing ball apertures 15 and entering tool receiving channel 16.

As shown in the exemplary embodiment illustrated in FIG. 6, the inner surface of interior collar channel 23 has tapered portion 25 which corresponds to securing ball apertures 15. As spring 40 exerts outward force on collar assembly 10, securing balls 60 in securing ball apertures 15 are forced to align with the outer-most, or narrowest, part of tapered portion 25. Retaining ring 30, in groove 18, is also pushed against stop-ridge 27 of house 20, which prevents collar assembly 10 from being forced too far outward by spring 40.

As a tool would be pushed into tool receiving channel 16, securing balls 60 freely rotate within securing ball apertures 15, allowing the tool shaft to proceed through tool receiving channel 16 and into tool guiding channel 54 (not shown). When a tool shaft is pushed into tool receiving channel 16, securing balls 60 are forced slightly towards the inner-most, or wider, part of tapered portion 25.

If the tool is pulled out from tool receiving channel 16, securing balls 60 are forced toward the outer-most, or narrowest, part of tapered portion 25, so that securing balls 60 are no longer able to freely rotate. The tool shaft is therefore locked within tool receiving channel 16.

To remove a tool from internal adapter 100, external collar base 11 is pressed inward toward handle 70. Spring 40 is compressed, and collar assembly 10 slides inward within interior collar channel 23. Securing ball apertures 15 align with the inner-most, or widest, part of tapered portion 25, which increases the volume of securing ball apertures 15. Securing balls 60 are then able to freely rotated within securing ball apertures 15, allowing the tool shaft to be pulled out of tool receiving channel 16.

As illustrated in FIG. 6, retaining ring 30 is secured in groove 18 with spring 40 positioned between and housed within house 20 and shaft driver assembly 50. The front portion of spring 40 rests against tubular sliding portion 14 around protuberance 17 and the rear portion of spring 40 rests against interior lip 57 of tool guiding channel 54 before transitional chamfer 55.

Figure 7:
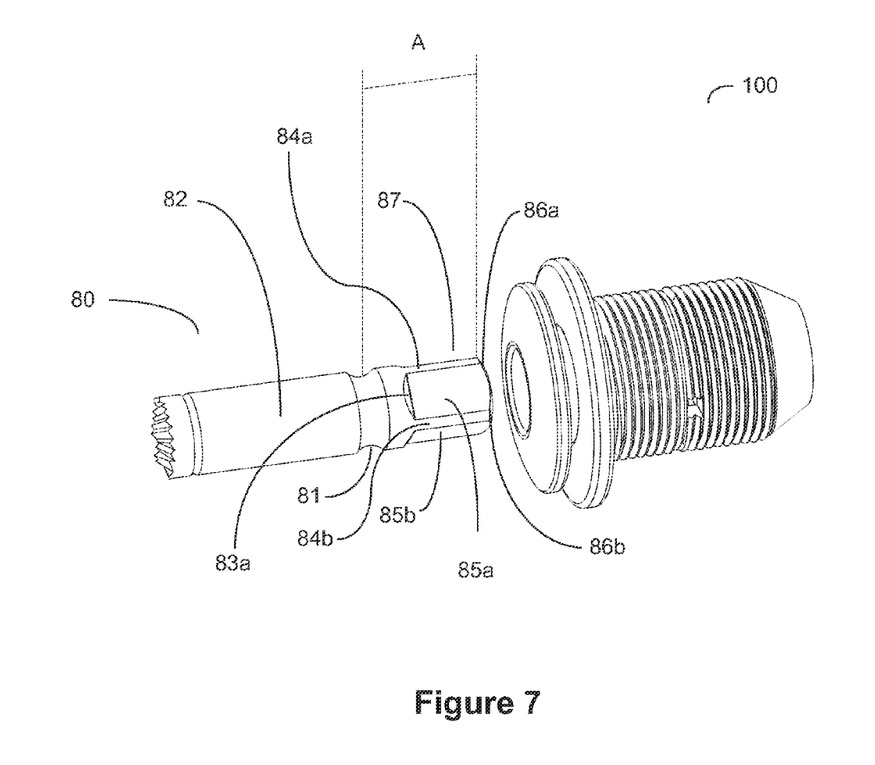
FIG. 7 is an exemplary embodiment of a tool shaft for use with a self-locking internal adapter.

FIG. 7 is an exemplary embodiment of tool shaft 82 for tool 80 which may be used with internal adapter 100. At one end of tool shaft 82 is handle-engaging portion 87. The opposite end of tool shaft 82 may contain any tool known in the art.

As illustrated in FIG. 7, groove 81 transitions tool shaft 82 to handle-engaging portion 87, which is squared with flat surfaces 85a, 85b (85c, 85d not shown). In further exemplary embodiments, handle-engaging portion may be hexagonal or any other configuration known in the art.

Flat surfaces 85a, 85b (85c, 85d not shown) each have a corresponding chamfer 83a (83b, 83c, 83d not shown) and are separated by rounded transitions 84a, 84b (84c, 84d not shown), each also have a corresponding chamfer 86a, 86b (86c, 86d not shown). The distance from the center of groove 81 and edge of chamfer 86a is labeled as A.

Figure 8A:
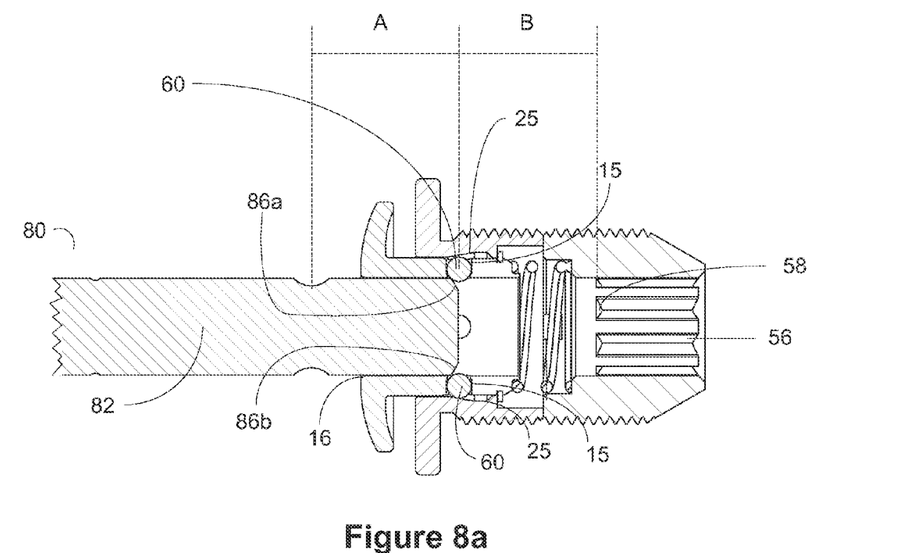
FIGS. 8a, 8b and 8c illustrate an exemplary embodiment of a self-locking internal adapter engaging an orthopedic tool.
Figure 8B:
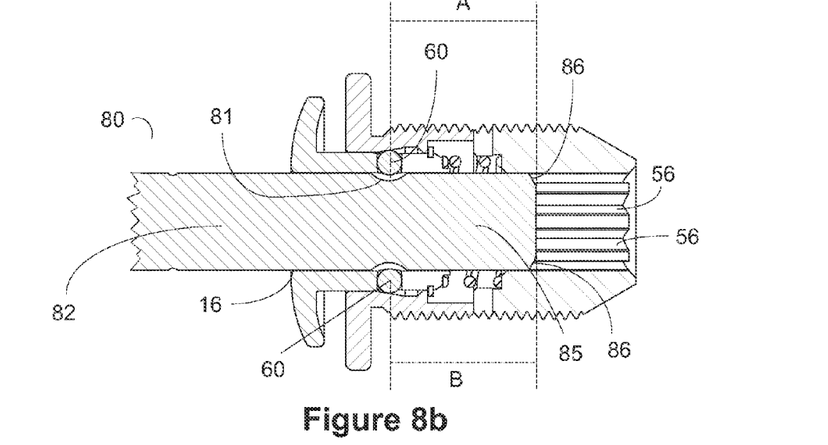
Figure 8C:
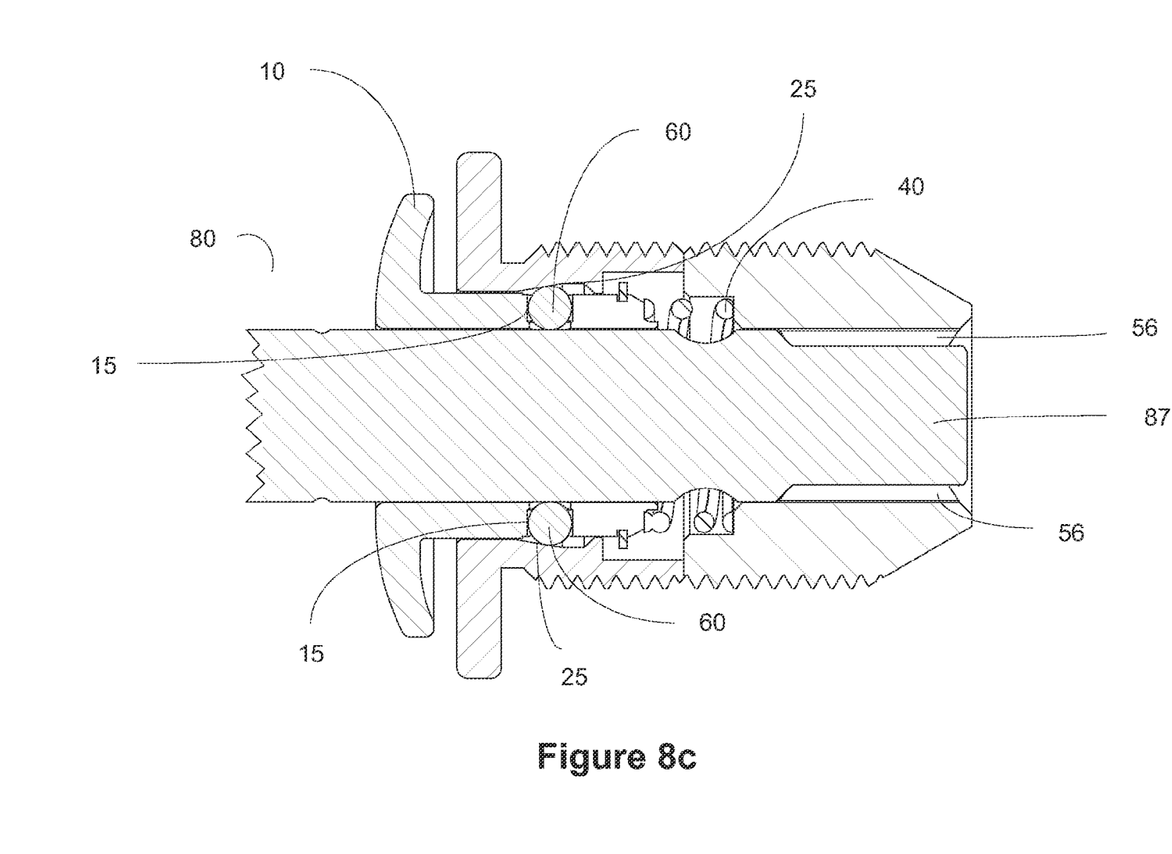

FIGS. 8a, 8b and 8c illustrate an exemplary embodiment of internal adapter 100 engaging tool 80.

As illustrated in FIG. 8a, tool 80 is partially inserted into internal adapter 100. Chamfers 86 engage securing balls 60 and force them into the larger area created by tapered portion 25. Securing balls 60 are able to freely rotate in securing ball apertures 15 (not shown) and tool shaft 82 is able to pass through tool receiving channel 16. The distance from the center of securing balls 60 to leading transition chamfer 58 of guiding chamfers 56 is labeled as B.

In the exemplary embodiment shown, distance A is equal to distance B. It is critical that distances A and B are equal to provide quick and secure locking of tool shaft 82 in internal adapter 100.

In FIG. 8b, tool shaft 82 is further in tool receiving channel 16, with groove 81 aligned with securing balls 60 and chamfers 86 aligned with leading transition chamfer 58 (not shown) of guiding chamfers 56. In order to fully secure tool shaft 82 in internal adapter 100, flat surfaces 85 must properly align with guiding chamfers 56. Securing balls 60 do not engage tool shaft 82 in this position, allowing tool shaft 82 to freely rotate within tool receiving channel 16 and be properly oriented to engage guiding chamfers 56.

FIG. 8c illustrates tool 80 secured within internal adapter 100. Tool shaft 82 is aligned so that handle-engaging portion 87 is aligned with guiding chamfers 56 to prevent rotational movement of tool 80 in handle 70 (not shown). Securing balls 60 are positioned along the portion of tapered surface 25 creating a smaller volume for securing ball apertures 15 and engage tool shaft 82 and prevent movement of tool 80 out of handle 70.

If tool 80 is pulled outward from handle 70, securing balls 60 are unable to rotate within securing ball apertures 15 and prevent movement of tool shaft 82. To release tool 80, collar assembly 10 is pushed inward toward handle 70 to compress spring 40. Securing balls 60 are aligned with the portion of tapered surface 25 creating a larger volume for securing ball apertures 15. Securing balls 60 are therefore able to freely rotate in securing ball apertures 15, allowing tool shaft 82 to be removed from internal adapter 100.

In the exemplary embodiment shown in FIG. 8c, chamfers 83 corresponding with flattened surfaces 85 correspond to and engage leading transition chamfers 58 to stabilize tool 80.

What is claimed is:

1. An orthopedic tool apparatus comprised of:
    at least one housing forming a handle and having an internal cavity; and
    at least one internal adapter comprised of
        a slidable collar assembly with an internal tool receiving channel, said collar assembly having a plurality of equidistant securing ball apertures and a retaining ring groove,
        a house assembly with an interior collar channel having a tapered surface creating a smaller interior collar channel diameter at the front of said interior collar channel and a larger interior collar channel diameter at the rear end of said interior collar channel and a stop-ridge, wherein said slidable collar assembly is slidable within said interior collar channel and said plurality of securing ball apertures are aligned with said tapered surface,
        a plurality of securing balls wherein each one of said plurality of securing balls engages one of said plurality of securing ball apertures to decrease the diameter of said internal tool receiving channel,
        a retaining ring contained in said retaining ring groove,
        a spring adapted to provide outward force on said slidable collar assembly so that said plurality of securing balls are aligned with said smaller interior collar channel diameter and said retaining ring engages stop-ridge to prevent outward movement of said slidable collar assembly,
        a shaft driver assembly having a plurality of guiding chamfers,
    wherein inward force applied to said slidable collar assembly aligns said plurality of securing balls with said larger interior collar channel diameter to increase the diameter of said tool receiving channel.

2. The apparatus of claim 1 wherein said internal handle cavity and said house assembly and said shaft driver assembly have corresponding threads.

3. The apparatus of claim 1 which has four securing balls and securing ball apertures.

4. The apparatus of claim 1 wherein said plurality of securing balls are freely rotatable in said securing ball apertures.

5. The apparatus of claim 1 wherein said guiding chamfers are double square.

6. The apparatus of claim 1 wherein said collar assembly includes an external collar base.

7. The apparatus of claim 1 wherein said shaft driver assembly and said internal cavity have corresponding tapered centralizing portions.

8. A handle for a medical shaft comprised of:

an integrally machined collar assembly having a collar base portion, an internal tool receiving channel and an internal tubular sliding portion with a groove and protuberance, wherein said internal tubular sliding portion contains four securing ball apertures symmetrically arranged around said tubular sliding portion;

an integrally machined house assembly comprised of an external house base and an interior collar channel with a stop-ridge, wherein said interior collar channel has a tapered portion of interior surface near the front of said interior collar channel;

wherein said internal tubular sliding portion of said collar assembly is slidingly engaged with said interior collar channel of said house assembly such that said four securing ball apertures are aligned with said tapered portion of said interior collar channel;

four securing balls, each engaged with and freely rotatable in one of said securing ball apertures, wherein said tapered portion of said interior collar channel secures said securing balls in said securing ball apertures;

a retaining ring contained in said groove, a spring having an inner diameter larger than the diameter of said protuberance on said internal tubular sliding portion allowing said spring to provide an outward force on said collar assembly, wherein outward movement of said collar assembly is prevented by said securing ring engaging said stop-ridge; and a shaft driver assembly securing said spring against said collar assembly, wherein said shaft driver assembly has a plurality of guiding chamfers corresponding to the flattened portions of an orthopedic tool;

wherein said collar assembly, said house assembly, said securing balls, said retaining ring, said spring and said shaft driver assembly are housed within a medical tool handle.

9. The apparatus of claim 8 wherein said medical tool handle and said shaft driver assembly contain corresponding tapered centralizing portions.

10. The apparatus of claim 8 wherein said house assembly and said shaft driver assembly contain outer threaded portions to engage said medical tool handle.

11. The apparatus of claim 8 wherein said securing ball apertures are contoured on their inward facing edge to have a diameter small than the diameter of said securing balls.

12. The apparatus of claim 8 wherein said collar base portion and said house base portion are external to said handle.

13. The apparatus of claim 8 wherein said shaft driver assembly has eight double-square guiding chamfers.

14. The apparatus of claim 8 wherein each of said guiding chamfers contains a stabilizing leading transition chamfer.

15. The apparatus of claim 8 wherein said medical handle is configured for use with a medical tool having a handle-engaging portion with a groove and a plurality of flattened surfaces separated by rounded transitions having corresponding chamfers, wherein the distance from the center of said groove to the leading edge of said corresponding chamfers is equal to the distance from the center of one of said securing balls to the leading edge of one of said guiding chamfers.

16. An orthopedic tool system comprised of:

an orthopedic tool handle having an inner handle cavity with a tapered rear portion;

an orthopedic tool having a shaft with a groove and a plurality of flattened surfaces having corresponding chamfers and separated by rounded transitions have corresponding chamfers; and an internal orthopedic tool adapter comprising an integrally machined collar assembly having a collar base portion, an internal tool receiving channel and an internal tubular sliding portion with a groove and a protuberance, wherein said internal tubular sliding portion contains four securing ball apertures contoured on their inward facing edge to have a smaller first diameter and symmetrically arranged around said tubular sliding portion;

an integrally machined house assembly comprised of an external house base and an interior collar channel with a stop-ridge, wherein said interior collar channel has a tapered portion of interior surface near the front of said interior collar channel creating a narrower diameter near said front of said interior collar channel and a larger diameter near the rear of said interior collar channel;

wherein said internal tubular sliding portion of said collar assembly is slidingly engaged with said interior collar channel of said house assembly such that said four securing ball apertures are aligned with said tapered portion of said interior collar channel;

four securing balls, each engaged with and freely rotatable in one of said securing ball apertures, wherein said tapered portion of said interior collar engaging channel secures said securing balls in said securing ball apertures and wherein said first smaller diameter is less than the diameter of said securing balls;

a retaining ring contained in said groove;

a spring having an inner diameter larger than the diameter of said protuberance on said internal tubular sliding portion allowing said spring to provide an outward force on said collar assembly, wherein outward movement of said collar assembly is prevented by said securing ring engaging said stop-ridge; and a shaft driver assembly securing said spring against said collar assembly, wherein said shaft driver assembly has a plurality of guiding chamfers corresponding to said flattened surfaces of said orthopedic tool and a tapered rear portion, wherein said guiding chamfers have leading transitional chamfers, wherein the distance from the center of said groove to the leading edge of said chamfers corresponding to said rounded transitions of said tool shaft is equal to the distance from the center of one of said securing balls to the leading edge of one of said leading transitional chamfers of said shaft driver assembly, wherein said internal orthopedic tool adapter is secured in said inner handle cavity and centralized by said tapered rear portion of said shaft driver assembly engaging said tapered rear portion of said internal handle cavity, and wherein said orthopedic tool is removable within said internal tool receiving channel, slidingly and rotationally secured by said securing balls engaging said shaft and centrally secured by said chamfers on said shaft which correspond to said rounded transitions engaging said leading transition chamfers of said shaft driver.

17. The system of claim 16 wherein said inner handle cavity is threaded and said house assembly and said shaft driver assembly have a corresponding threaded exterior surface.

18. The system of claim 16 wherein the distance from the center of said groove on said orthopedic tool to leading edge of said chamfers corresponding to said rounded transitions is equal to the distance from the center of one of said securing balls to the leading edge of one of said guiding chamfers.

19. The system of claim 16 wherein inward force applied to said slidable collar assembly aligns said securing balls with said larger interior collar channel diameter to increase the diameter of said receiving channel.

20. The system of claim 16 wherein said securing balls are freely rotatable and disengaged from said tool shaft at said groove.

\* \* \* \* \*